United States Patent
Speake et al.

(10) Patent No.: US 11,512,088 B2
(45) Date of Patent: Nov. 29, 2022

(54) SYNTHETIC PROCESS AND INTERMEDIATES

(71) Applicant: Avista Pharma Solutions, Inc., Durham, NC (US)

(72) Inventors: Jason D. Speake, Winston-Salem, NC (US); Joe B. Perales, Durham, NC (US); Brent Christopher Beck, Apex, NC (US); Bharathi Pandi, Cary, NC (US)

(73) Assignee: AVISTA PHARMA SOLUTIONS, INC., Durham, NC (US)

( * ) Notice: Subject to any disclaimer, the term of this patent is extended or adjusted under 35 U.S.C. 154(b) by 0 days.

(21) Appl. No.: 16/775,451

(22) Filed: Jan. 29, 2020

(65) Prior Publication Data

US 2020/0239481 A1   Jul. 30, 2020

Related U.S. Application Data

(60) Provisional application No. 62/798,735, filed on Jan. 30, 2019.

(51) Int. Cl.
 *C07D 487/04*   (2006.01)
(52) U.S. Cl.
 CPC ................. *C07D 487/04* (2013.01)

(58) Field of Classification Search
 CPC .................................................. C07D 487/04
 See application file for complete search history.

(56) References Cited

FOREIGN PATENT DOCUMENTS

| CN | 104649945 A | 5/2015 |
| WO | 2003087061 A1 | 10/2003 |
| WO | 2011041713 A2 | 4/2011 |
| WO | WO-2019245590 A1 * | 12/2019 ........... C07D 487/04 |

OTHER PUBLICATIONS

International Search Report for PCT/US2020/015556, dated May 29, 2020.
Nakao, K., et al., "CJ-023, 423, a novel, potent and selective prostaglandin EP4 receptor antagonist with antihyperalgesic properties". The Journal of Pharmacology and Experimental Therapeutics (2007), vol. 322, No. 2, pp. 686-694.
De Vito, V., et al., "Detection and quantification of the selective EP4 receptor antagonist CJ-023423 (grapiprant) in canine plasma by HPLC with spectrofluorimetric detection", Journal of Pharmaceutical and Biomedical Analysis (2016), vol. 118, pp. 251-258.

* cited by examiner

*Primary Examiner* — John S Kenyon
(74) *Attorney, Agent, or Firm* — Barnes & Thornburg, LLP

(57) ABSTRACT

The present disclosure describes a synthetic process and novel intermediates related to spirocyclic azetidenyl-isobenzofuran derivatives having an isothiazoline moiety, which are useful as antiparasitics.

7 Claims, No Drawings

SYNTHETIC PROCESS AND INTERMEDIATES

CROSS-REFERENCE TO RELATED APPLICATIONS

The present application claims the benefit of U.S. Provisional Application Ser. No. 62/798,735, filed Jan. 30, 2019, herein incorporated by reference in its entirety.

FIELD OF THE INVENTION

The present disclosure describes a synthetic process and novel intermediates related to prostaglandin EP4 receptor antagonists, which are useful in the treatment or alleviation of pain and inflammation and other inflammation-associated disorders, such as arthritis, treating or preventing disorders or medical conditions selected from pain, inflammatory diseases and the like.

BACKGROUND

Rheumatoid arthritis (RA) is an immune-mediated, systemic inflammatory disease that affects mainly synovial joins, with intra-articular inflammation, synovial hyperplasia and progressive degradation of cartilage and bone. Prevalence of the disease is about 1% of the population, and the disease is more frequent (and perhaps worse) in women than in men. There have been clear advances in the pharmacological management of rheumatoid arthritis over the last decade, but many patients still do not tolerate or do not respond well to the available therapies.

Moreover, the control and management of arthritis associated pain and inflammation in animals, such as companion animals, specifically in dogs, is also an area of growing interest. Many FDA-approved drugs are available to treat pain associated with osteoarthritis (OA) in dogs (e.g., carprofen, firocoxib, meloxicam, deracoxib, and robenacoxib), all of which work by inhibiting cyclooxygenase enzymes. The FDA approved COX inhibitor NSAIDs for use in dogs, unless contra-indicated, are considered to be effective treatments for the pain associated with RA. These COX-inhibiting NSAIDs, as a class, however, carry the potential for adverse effects including gastrointestinal ulceration and perforation, and renal insufficiency. The Food and Drug Administration (FDA) has required language in the precaution section of the package inserts of these drugs warning that, as a class, they may be associated with renal, gastrointestinal (GI), and hepatic toxicity. Specifically, labels of these drugs warn of the "potential to produce GI ulceration and/or GI perforation".

Prostaglandins are mediators of pain, fever and other symptoms associated with inflammation. Especially prostaglandin E2 (PGE2) is the predominant eicosanoid detected in inflammation conditions. In addition, it is also involved in various physiological and/or pathological conditions and such as hyperalgesia, uterine contraction, digestive peristalsis, awakeness, suppression of gastric acid secretion, blood pressure, platelet function, bone metabolism, angiogenesis or the like.

Four PGE2 receptor subtypes (EP1, EP2, EP3 and EP4) displaying different pharmacological properties have been cloned. EP4 subtype, a Gs-coupled receptor stimulates cAMP production, and is distributed in a wide variety of tissue suggesting a major role in PGE2-mediated biological events.

Among the multiple targets involved in the pathogenesis of rheumatoid arthritis, the prostaglandin E2 receptor 4 (EP4) subtype receptor of prostaglandin E2 (PGE2) is one of the most promising because, unlike common NSAIDs that inhibit the synthesis of prostaglandins, selective EP4 antagonists have the potential to combine immunomodulatory and direct anti-inflammatory properties. Furthermore, the EP4 receptor in mice, humans and dogs has been cloned and characterized and the canine EP4 receptor has approximately 90% homology to the human receptor. EP4 antagonists present an opportunity for a novel pharmaceutical or veterinary therapy.

Grapiprant, whose chemical name is N-[[[2-[4-(2-Ethyl-4,6-dimethyl-1H-imidazo[4,5-c]pyridin-1-yl)phenyl]ethyl]amino]carbonyl]-4 methylbenzenesulfonamide, and sold under the tradename Galliprant®, is a prostaglandin E2 (PGE2) EP4 receptor antagonist; a non-cyclooxygenase (COX) inhibiting, non-steroidal anti-inflammatory drug (NSAID) in the piprant class. Grapiprant is indicated for the control of pain and inflammation associated with osteoarthritis (OA) in dogs. Further reference is made to WO 2002/032422, WO 2002/032900, WO 2006/095268, as well as WO 2003/086371, WO 2011/102149, and WO 2014/148053. Additional background research regarding compounds with an imidazopyridine or imidazopyrazine core ring structure include US 2013/195848, WO 2014/078813, WO 2011/151259, WO 2011/113862, US 2005/0009832, US 2004/0220189, WO 2006/091671, and WO 2018/013430. All of these cited patent publications are incorporated by reference with regard to their background teaching.

Despite this background of research and development, there remains a need for novel EP4 antagonists to offer safe and effective pharmaceutical or veterinary therapy. PCT/US2018/046142, herein incorporated by reference in its entirety, describes novel imidazopyridine/pyrazine derivatives with activity as prostaglandin EP4 receptor antagonists. More specifically, the imidazopyridine/pyrazine derivatives, including veterinary or pharmaceutically acceptable salts thereof, are represented by Formula (I):

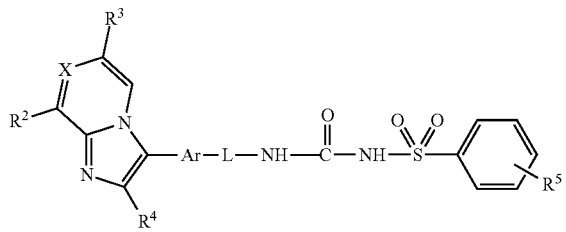

Formula (I)

wherein
X is N or $CR^1$, where each $R^1$ individually is hydrogen, halogen, CN, $C_{1-3}$ alkyl, or $C_{1-3}$ haloalkyl;
$R^2$ is hydrogen, $C_{1-3}$ alkyl, or $C_{1-3}$ haloalkyl;
$R^3$ is hydrogen, $C_{1-3}$ alkyl, or $C_{1-3}$ haloalkyl;
$R^4$ is hydrogen, $C_{1-3}$ alkyl, $C_{1-3}$ haloalkyl, or $C_{3-6}$ cycloalkyl;
$R^5$ is hydrogen, halogen, CN, $C_{1-3}$ alkyl, or $C_{1-3}$ haloalkyl;
Ar is phenyl, pyridyl, or thiophenyl, each optionally substituted with one or more halogen, CN, $NO_2$, $NH_2$, $N(C_{1-3}$ alkyl$)_2$, OH, $OC_{1-3}$ alkyl, $C_{1-3}$ alkyl, or $C_{1-3}$ haloalkyl; and
L is —$CH_2CH_2$—, —$CH_2CH_2CH_2$—, or —$OCH_2C$.

One embodiment described is a compound 1-[2-[4-(2-ethyl-6,8-dimethyl-imidazo[1,2-a]pyrazin-3-yl)phenyl]

ethyl]-3-(p-tolylsulfonyl) urea, or a veterinary or pharmaceutically acceptable salt thereof.

SUMMARY

The present disclosure describes a synthetic process for the compounds of Formula (I) of PCT/US2018/046142, for example, in particular for the compound 1-[2-[4-(2-ethyl-6, 8-dimethyl-imidazo[1,2-a]pyrazin-3-yl)phenyl]ethyl]-3-(p-tolylsulfonyl) urea, or a veterinary or pharmaceutically acceptable salt thereof.

One embodiment includes a compound selected from 4-methyl-N-((4-(4,4,5,5-tetramethyl-1,3,2-dioxaborolan-2-yl)phenethyl)carbamoyl)benzenesulfonamide; 2-ethyl-6,8-dimethylimidazo[1,2-a]pyrazine; or 3-bromo-2-ethyl-6,8-dimethylimidazo[1,2-a]pyrazine, or a veterinary or pharmaceutically acceptable salt thereof. Each of these compounds is believed to be a useful intermediate in the synthesis of a final product useful as an EP4 antagonist.

One embodiment includes a process for making 1-[2-[4-(2-ethyl-6,8-dimethyl-imidazo[1,2-a]pyrazin-3-yl)phenyl]ethyl]-3-(p-tolylsulfonyl)urea or a salt thereof comprising using 4-methyl-N-((4-(4,4,5,5-tetramethyl-1,3,2-dioxaborolan-2-yl)phenethyl)carbamoyl)benzenesulfonamide.

One embodiment includes a process for making a compound of Formula (II) or a salt thereof:

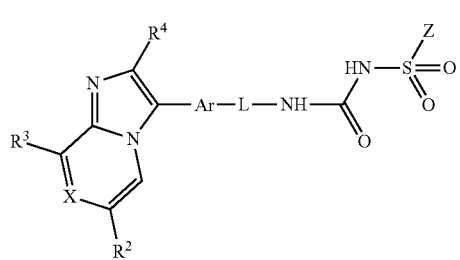

Formula (II)

wherein:
X is N or $CR^1$, where $R^1$ is hydrogen, halogen, CN, $C_{1-3}$ alkyl, or $C_{1-3}$ haloalkyl;
$R^2$ is hydrogen, halogen, $C_{1-3}$ alkyl, $C_{1-3}$ haloalkyl, CN, aryl, or heteroaryl;
$R^3$ is hydrogen, halogen, $C_{1-3}$ alkyl, $C_{1-3}$ haloalkyl, or CN;
$R^4$ is hydrogen, $C_{1-3}$ alkyl, $C_{1-3}$ haloalkyl, $C_{3-6}$ cycloalkyl, heterocyclyl, heteroaryl, or aryl;
Z is phenyl or $C_{3-7}$ cycloalkyl, each substituted with one or more $R^5$, where $R^5$ is hydrogen, halogen, CN, $C_{1-3}$ alkyl, $C_{1-3}$ haloalkyl, $C_{1-3}$ haloalkoxy, or $C_{1-3}$ alkoxy;
Ar is phenyl, pyridyl, or thiophenyl, each optionally substituted with one or more halogen, CN, $NO_2$, $NH_2$, $N(C_{1-3}$ alkyl$)_2$, OH, $C_{1-3}$ alkoxy, $C_{1-3}$ alkyl, or $C_{1-3}$ haloalkyl; and
L is $CH_2CH_2$, $CH_2CH_2CH_2$, or $OCH_2CH_2$,
comprising:
cyclizing a compound of formula (a):

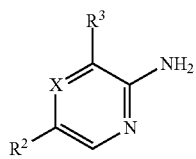

formula (a)

wherein:
X is N or $CR^1$, where $R^1$ is hydrogen, halogen, CN, $C_{1-3}$ alkyl, or $C_{1-3}$ haloalkyl;
$R^2$ is hydrogen, halogen, $C_{1-3}$ alkyl, $C_{1-3}$ haloalkyl, CN, aryl, or heteroaryl; and
$R^3$ is hydrogen, halogen, $C_{1-3}$ alkyl, $C_{1-3}$ haloalkyl, or CN; halogenating the resulting cyclized product to form a compound of formula (b):

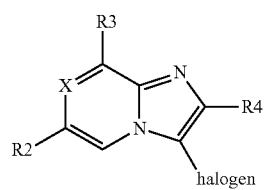

formula (b)

wherein $R^4$ is hydrogen, $C_{1-3}$ alkyl, $C_{1-3}$ haloalkyl, $C_{3-6}$ cycloalkyl, heterocyclyl, heteroaryl, or aryl; and
treating a compound of formula (b) with a compound of formula (c):

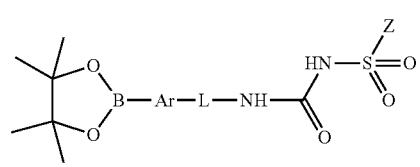

formula (c)

wherein
Z is phenyl substituted with $R^5$, where $R^5$ is hydrogen, halogen, CN, $C_{1-3}$ alkyl, $C_{1-3}$ haloalkyl, $C_{1-3}$ haloalkoxy, or $C_{1-3}$ alkoxy;
Ar is phenyl, pyridyl, or thiophenyl, each optionally substituted with one or more halogen, CN, $NO_2$, $NH_2$, $N(C_{1-3}$ alkyl$)_2$, OH, $C_{1-3}$ alkoxy, $C_{1-3}$ alkyl, or $C_{1-3}$ haloalkyl; and
L is $CH_2CH_2$, $CH_2CH_2CH_2$, or $OCH_2CH_2$,
to form a compound of Formula (II).

In one aspect, X is N, $R^2$ is $C_{1-3}$ alkyl, $R^3$ is $C_{1-3}$ alkyl, $R^4$ is $C_{1-3}$ alkyl, Ar is phenyl, L is $CH_2CH_2$, Z is phenyl substituted with one $R^5$. In one aspect $R^2$ is methyl, $R^3$ is methyl, $R^4$ is ethyl, Ar is unsubstituted phenyl, and $R^5$ is $C_{1-3}$ alkyl. In one aspect, $R^5$ is methyl. In one aspect, the compound of formula (c) is 4-methyl-N-((4-(4,4,5,5-tetramethyl-1,3,2-dioxaborolan-2-yl)phenethyl)carbamoyl)benzenesulfonamide. In one aspect, the compound of Formula (II) is 1-[2-[4-(2-ethyl-6,8-dimethyl-imidazo[1,2-a]pyrazin-3-yl)phenyl]ethyl]-3-(p-tolylsulfonyl)urea.

As herein described, the synthetic process herein described is useful in the preparation of compounds that are described in U.S. Provisional Application No. 62/798,738 and its progeny, which are hereby incorporated by reference in their entirety.

The compound, 1-[2-[4-(2-ethyl-6,8-dimethyl-imidazo[1,2-a]pyrazin-3-yl)phenyl]ethyl]-3-(p-tolylsulfonyl) urea, which may be referred to as Compound A, is useful for treating pain, such as one or more of joint pain, musculoskeletal pain, lower back pain, neck pain, skeletal pain, sprain, strain, myositis, neuralgia, fibromyalgia, synovitis, arthritis, rheumatoid arthritis, degenerative joint disease, osteoarthritis, gout, ankylosing spondylitis, and bursitis. One aspect of these embodiments includes where the subject is a mammal. One aspect of these embodiments includes where the mammal is a companion animal.

One or more aspects and embodiments may be incorporated in a different embodiment although not specifically described. That is, all aspects and embodiments may be combined in any way or combination.

DETAILED DESCRIPTION

The present disclosure describes a synthetic process for Compounds of Formula (I) and (II), in particular, for the compound 1-[2-[4-(2-ethyl-6,8-dimethyl-imidazo[1,2-a]pyrazin-3-yl)phenyl]ethyl]-3-(p-tolylsulfonyl) urea, or a veterinary or pharmaceutically acceptable salt thereof.

The preparation of Compound A or a veterinary acceptable salt thereof may be accomplished via the route and intermediates described in PCT/US2018/046142. As an alternative for manufacturing scale, however, the preparation of compounds of Formula (I) and (II), including Compound A, or salts thereof, may be accomplished via the route and intermediates shown hereinbelow.

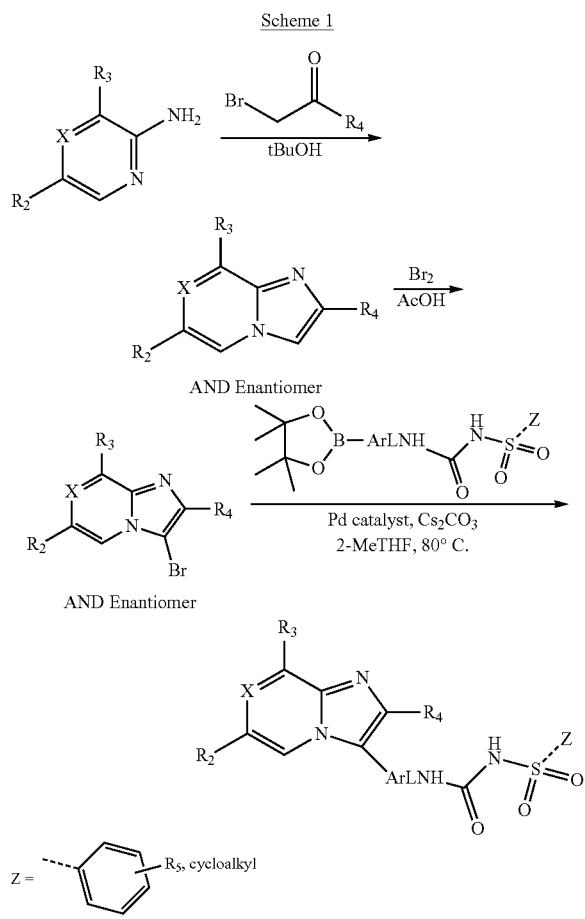

Scheme 1 describes a general process for preparing compounds of Formula (I) and (II), and specifically Compound A, wherein X is N or $CR^1$, where each $R^1$ individually is hydrogen, halogen, CN, $C_{1-3}$ alkyl, or $C_{1-3}$ haloalkyl;

$R^2$ is hydrogen, $C_{1-3}$ alkyl, $C_{1-3}$ haloalkyl, halogen, CN, aryl, or heteroaryl;

$R^3$ is hydrogen, $C_{1-3}$ alkyl, halogen, CN, or $C_{1-3}$ haloalkyl;
$R^4$ is hydrogen, $C_{1-3}$ alkyl, $C_{1-3}$ haloalkyl, or $C_{3-6}$ cycloalkyl, heteroaryl, heterocyclyl, or aryl;
$R^5$ is hydrogen, halogen, CN, $C_{1-3}$ alkyl, or $C_{1-3}$ haloalkyl, $C_{1-3}$ haloalkoxy, or $C_{1-3}$ alkoxy;
Ar is phenyl, pyridyl, or thiophenyl, each optionally substituted with one or more halogen, CN, $NO_2$, $NH_2$, $N(C_{1-3}$ alkyl$)_2$, OH, $OC_{1-3}$ alkyl, $C_{1-3}$ alkyl, or $C_{1-3}$ haloalkyl; and
L is —$CH_2CH_2$—, —$CH_2CH_2CH_2$—, or —$OCH_2CH_2$—.

As used herein the phrase veterinary or veterinarily or pharmaceutical or pharmaceutically acceptable salt refers to any salt of a compound disclosed herein which retains its biological properties and which is not toxic or otherwise undesirable for veterinary or pharmaceutical use. Certain compounds of the present invention have sites that would allow for a veterinary or veterinarily, or pharmaceutical or pharmaceutically acceptable salt, and such salt forms are also included in the present invention. Such salts may be derived from a variety of organic and inorganic counter-ions known in the art. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and like acids.

Salts further include, by way of example only, salts of non-toxic organic or inorganic acids, such as halides, such as, chloride and bromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

Examples of inorganic bases that can be used to form base addition salts include, but are not limited to, metal hydroxides, such as lithium hydroxide, sodium hydroxide, and potassium hydroxide; metal amides, such as lithium amide and sodium amide; metal carbonates, such as lithium carbonate, sodium carbonate, and potassium carbonate; and ammonium bases such as ammonium hydroxide and ammonium carbonate.

Examples of organic bases that can be used to form base addition salts include, but are not limited to, metal alkoxides, such as lithium, sodium, and potassium alkoxides including lithium methoxide, sodium methoxide, potassium methoxide, lithium ethoxide, sodium ethoxide, potassium ethoxide, and potassium tert-butoxide; quaternary ammonium hydroxides, such as choline hydroxide; and amines including, but not limited to, aliphatic amines (i.e., alkylamines, alkenylamines, alkynylamines, and alicyclic amines), heterocyclic amines, arylamines, heteroarylamines, basic amino acids, amino sugars, and polyamines.

According to embodiments of the present invention, the base can be a quaternary ammonium hydroxide, wherein one or more of the alkyl groups of the quaternary ammonium ion are optionally substituted with one or more suitable substituents. Preferably, at least one alkyl group is substituted with one or more hydroxyl groups. Non-limiting examples of quaternary ammonium hydroxides that can be used in accordance with the present invention include choline hydroxide, trimethylethylammonium hydroxide, tetramethylammonium hydroxide, and is preferably choline hydroxide. According to embodiments of the present invention, an alkylamine base can be substituted or unsubstituted. Non-limiting examples of unsubstituted alkylamine bases that can be used in accordance with the present invention include methylamine, ethylamine, diethylamine, and triethylamine. A substituted alkylamine base is preferably substituted with one or more hydroxyl groups, and preferably one to three hydroxyl groups. Non-limiting examples of substituted alkylamine bases that can be used in accordance with the present invention include 2-(diethylamino)ethanol, N,N-dimethylethanolamine (deanol), tromethamine, ethanolamine, and diolamine.

As used herein, the terms "subject" and "patient" are used interchangeably herein. The terms "subject" and "subjects" refer to a primate such as a monkey such as a cynomolgus monkey, a chimpanzee, and a human or non-primate animal. In one embodiment, the subject is a human. In another embodiment, the subject is a companion animal such as a dog or cat. In a further embodiment, the subject is an animal of agricultural importance such as a sheep, cow, horse, goat, fish, pig, or domestic fowl (such as a chicken, turkey, duck, or goose).

In addition, certain compounds of the present invention have substituent groups that would allow for a pharmaceutically acceptable prodrug moiety, and such prodrug forms are also included in the present invention. A pharmaceutically acceptable prodrug refers to a compound having a group which may be converted into an amino group, a hydroxyl group, a carboxyl group, or the like, by solvolysis or under a physiological condition. Examples of the groups forming the prodrug include those as described in Prog. Med., 5, 2157-2161 (1985) or "Pharmaceutical Research and Development" (Hirokawa Publishing Company, 1990), vol. 7, Drug Design, 163-198. The term prodrug is used throughout the specification to describe any pharmaceutically acceptable form of a compound, which upon administration to a patient, provides the active compound. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that may be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The present invention includes all pharmaceutically acceptable isotopically-labelled compounds of the invention wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labelled compounds of the invention, such as those incorporating a radioactive isotope, may be useful in drug or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, may be useful in Positron Emission Topography (PET) studies for examining substrate receptor occupancy. Isotopically-labelled compounds of the invention may generally be prepared by conventional techniques known to those skilled in the art or by processes analogous to those described in the accompanying Examples and Preparations using an appropriate isotopically-labelled reagents in place of the non-labelled reagent previously employed.

In certain cases, the depicted substituents can contribute to optical and/or stereoisomerism. Compounds having the same molecular formula but differing in the nature or sequence of bonding of their atoms or in the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers". When a compound has an asymmetric center, for example when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, Angew. Chem. 78: 413-447, Angew. Chem., Int. Ed. Engl. 5: 385-414 (errata: Angew. Chem., Int. Ed. Engl. 5:511); Prelog and Helmchen, 1982, Angew. Chem. 94: 614-631, Angew. Chem. Internat. Ed. Eng. 21: 567-583; Mata and Lobo, 1993, Tetrahedron: Asymmetry 4: 657-668) or can be characterized by the manner in which the molecule rotates the plane of polarized light and is designated dextrorotatory or levorotatory (namely, as (+)- or (−)-isomers, respectively). A chiral compound can exist as either an individual enantiomer or as a mixture thereof. A mixture containing equal proportions of enantiomers is called a "racemic mixture".

In certain embodiments, the compounds disclosed herein can possess one or more asymmetric centers; and such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art.

In certain embodiments, the compounds disclosed herein are "stereochemically pure". A stereochemically pure compound has a level of stereochemical purity that would be recognized as "pure" by those of skill in the art. Of course, this level of purity may be less than 100%. In certain embodiments, "stereochemically pure" designates a compound that is substantially free, i.e. at least about 85% or more, of alternate isomers. In particular embodiments, the compound is at least about 85%, about 90%, about 91%, about 92%, about 93%, about 94%, about 95%, about 96%, about 97%, about 98%, about 99%, about 99.5% or about 99.9% free of other isomers.

COMPOSITIONS AND METHODS OF ADMINISTRATION

Compound A or a veterinary or pharmaceutically acceptable salt thereof, made in the methods disclosed herein, may be administered in certain embodiments using veterinary or pharmaceutical compositions including at least one compound of Formula (I) or (II), if appropriate in the salt form, either used alone or in the form of a combination with one or more compatible and veterinarily or pharmaceutically acceptable carriers, such as diluents or adjuvants, or with another agent. There are provided compositions which comprise Compound A or a veterinary or pharmaceutically acceptable salt thereof, and an acceptable excipient, carrier, or diluent. The composition may also be in a variety of forms, including, but are not limited to, oral formulations, injectable formulations, and topical, dermal or subdermal formulations.

The composition may be in a form suitable for oral use, for example, as dietary supplements, troches, lozenges, chewables, tablets, hard or soft capsules, emulsions, aqueous or oily suspensions, aqueous or oily solutions, dispersible powders or granules, syrups, or elixirs. Compositions intended for oral use may be prepared according to any method known in the art for the manufacture of veterinary, pharmaceutical, or pesticidal compositions and such compositions may contain one or more agents selected from the group consisting of sweetening agents, bittering agents, flavoring agents, coloring agents and preserving agents in order to provide elegant and palatable preparations.

Tablets may contain the active ingredient in admixture with non-toxic, pharmaceutically acceptable excipients, which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example, peanut oil, liquid paraffin, or olive oil.

The compositions may also be in the form of oil-in-water or water-in-oil emulsions. The oily phase may be a vegetable oil, for example, olive oil or arachis oil, or a mineral oil, for example, liquid paraffin or mixtures of these. Suitable emulsifying agents may be naturally occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and preservatives.

In one embodiment of the formulation, the composition is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids. Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously. In one embodiment of the oily phase, the oily phase may be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example, $C_8$-$C_{10}$ caprylic/capric triglyceride. In another embodiment, the oily phase will represent a % v/v range selected from the group consisting of about 2 to about 15%; about 7 to about 10%; and about 8 to about 9% v/v of the microemulsion. The aqueous phase includes, for example, water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion. Surfactants for the microemulsion include diethylene glycol monoethyl ether, dipropylene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol. Some compounds are common to the three components discussed above, for example, aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2.

In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an antioxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxypropylmethylcellulose, sodium alginate, polvinylpyrrolidone, gum tragacanth and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example, polyethylene sorbitan monooleate. The aqueous suspensions may also contain one or more preservatives, for example, ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s), and coloring agent(s).

The compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Co-solvents such as ethanol, propylene glycol or polyethylene glycols may also be used. Preservatives, such as phenol or benzyl alcohol, may be used.

In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Topical, dermal and subdermal formulations may include emulsions, creams, ointments, gels or pastes or 'spot-on' formulations.

Organic solvents that may be used in the invention include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, compositions of the present invention may include plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$-$C_{12}$) triglycerides.

Dosage forms may contain from about 0.5 mg to about 5 g of an active agent.

In one embodiment of the invention, the active agent is present in the formulation at a concentration of about 0.05 to 10% weight/volume.

The compounds of Formula (I) or (II) may be employed as such or in the form of their preparations or formulations as combinations with other active substances, such as, for example, other such as, for example, EP4 antisense nucleic acids, amino acids, peptides, carbohydrates, anti-EP4 antibodies, COX-2 selective, COX-1 selective or non-selective NSAIDs, opioids, local anesthetics, disease-modifying, antirheumatoid drugs, or steroids. The combinations may be part of the same formulation or may be administered separately or sequentially to the locus.

The compounds of Formula (I) and (II) are useful for treating pain, such as one or more of joint pain, musculoskeletal pain, lower back pain, neck pain, skeletal pain, sprain, strain, myositis, neuralgia, fibromyalgia, synovitis, arthritis, rheumatoid arthritis, degenerative joint disease, osteoarthritis, gout, ankylosing spondylitis, and bursitis.

The compounds of Formula (I) and (II) may be combined with one or more agents having the same sphere of activity, for example, to increase activity, or with substances having another sphere of activity, for example, to broaden the range of activity. Any of the individually listed agents may be used in combination with compounds of Formula (I) and (II) along with any other one or more listed agents independently.

Suitable agents for combination therapy include, whereby one or more compounds of Formula (I) and (II) may be employed as such or in the form of their preparations or formulations as combinations with one or more other veterinary or pharmaceutically active substances, such as, for example, EP4 antisense nucleic acids, amino acids, peptides, carbohydrates, anti-EP4 antibodies, COX-2 selective, COX-1 selective or non-selective NSAIDs, opioids, local anesthetics, disease-modifying, anti-rheumatoid drugs, or steroids. The combinations may be part of the same formulation or may be administered separately or sequentially.

A pharmaceutical preparation comprising a compound of Formula (I) and (II), for example, Compound A or a veterinary or pharmaceutically acceptable salt thereof for delivery to a human or other mammal, is preferably in unit dosage form, in which the preparation is subdivided into unit doses containing an appropriate quantity of the active component. The unit dosage form may be a packaged preparation containing discrete quantities of the preparation, such as packaged tablets, capsules, and powders in vials or ampoules. Also, the unit dosage form may be a capsule, tablet or lozenge itself, or it may be an appropriate number of any of these in packaged form.

The quantity of active component in a unit dose preparation may be varied or adjusted from about 0.1 mg to about 1000 mg, according to the particular application and the potency of the active component. The composition may, if desired, also contain other compatible therapeutic agents.

In therapeutic use for the treatment or prevention of pain in a human or other mammal, the compounds utilized in the method of treatment are administered at an initial dosage of about 0.1 mg/kg to about 100 mg/kg per interval. Preferred intervals may be daily, weekly, semi-monthly, monthly, bi-monthly, quarterly, tri-annually, semi-annually, or annually. The dosages may be varied depending on the requirements of the patient, for example, the size of the human or mammal being treated, the severity of the condition being treated, the route of administration, and the potency of the compound(s) being used. Determination of the proper dosage and route of administration for a particular situation is within the skill of the practitioner. Generally, the treatment will be initiated with smaller dosages which are less than the optimum dose of the compound, which may be increased in small increments until the optimum effect under the particular circumstances is reached. For convenience, the total daily dosage may be divided and administered in portions during the day if desired.

Compound A, and compositions comprising a therapeutically effective amount of Compound A, an acceptable salt thereof, and a veterinary or pharmaceutically acceptable excipient, diluent, or carrier are useful as method for treating pain comprising administering to a subject in need thereof an effective amount of a compound of the present invention. Additionally, Compound A may be used in therapy. Additionally, Compound A may be useful in the manufacture of a medicament for the treatment of pain. Additionally, Compound A may be used for the treatment of pain. One aspect of these embodiments includes where the subject is a mammal. One aspect of these embodiments includes where the mammal is a companion animal. One aspect of these embodiments includes where the pain is associated with one or more of joint pain, musculoskeletal pain, lower back pain, neck pain, skeletal pain, sprain, strain, myositis, neuralgia, fibromyalgia, synovitis, arthritis, rheumatoid arthritis, degenerative joint disease, osteoarthritis, gout, ankylosing spondylitis, and bursitis.

Compound A or a veterinary or pharmaceutically acceptable salt thereof, or a suitable combination of Compound A or a veterinary or pharmaceutically acceptable salt thereof and optionally, with at least one additional veterinary or pharmaceutical agent may be administered directly to the animal and/or indirectly by applying it to the local environment in which the animal dwells (such as bedding, enclosures, and the like). Direct administration includes contacting the skin, fur, or feathers of a subject animal with the compound(s), or by feeding or injecting the compounds into the animal.

EXAMPLES

Experimental Procedures

Liquid chromatography-mass spectrometry (LCMS) experiments to determine retention times and associated mass ions were performed using one or more of the following Methods A, B, and C:

Method A: Waters BEH (ethylene bridged hybrid) $C_{18}$ column, 3.0×30 mm, 1.7 μm, was used at a temperature of 50° C. and at a flow rate of 1.5 mL/min, 2 μL injection, mobile phase: (A) water with 0.1% formic acid and 1% acetonitrile, mobile phase; (B) MeOH with 0.1% formic acid; retention time given in minutes. Method A details: (I) ran on a Binary Pump G1312B, Agilent Technologies, with UV/Vis diode array detector G1315C and Agilent 6130 mass spectrometer in positive and negative ion electrospray mode with UV PDA detection with a gradient of 15-95% (B) in a 2.2 min linear gradient (II) hold for 0.8 min at 95% (B) (III) decrease from 95-15% (B) in a 0.1 min linear gradient (IV) hold for 0.29 min at 15% (B);

Method B: An Agilent Zorbax Bonus RP column, 2.1×50 mm, 3.5 μm, was used at a temperature of 50° C. and at a flow rate of 0.8 mL/min, 2 μL injection, mobile phase: (A) water with 0.1% formic acid and 1% acetonitrile, mobile phase (B) MeOH with 0.1% formic acid; retention time given in minutes. Method B details: (I) ran on a Binary Pump G1312B, Agilent Technologies, with UV/Vis diode array detector G1315C and Agilent 6130 mass spectrometer in positive and negative ion electrospray mode with UV-detection at 220 and 254 nm with a gradient of 5-95% (B) in a 2.5 min linear gradient (II) hold for 0.5 min at 95% (B) (III) decrease from 95-5% (B) in a 0.1 min linear gradient (IV) hold for 0.29 min at 5% (B).

Method C: An API 150EX mass spectrometer, Applied Biosystems, linked to a Shimadzu LC-10AT liquid chromatography system, with a diode array detector was used. The spectrometer had an electrospray source operating in positive and negative ion mode. The liquid chromatography was carried out using an Agilent ZORBAX XDB 50×2.1 mm $C_{18}$ column and a 0.5 mL/minute flow rate. Method C details: Solvent A: 95% water, 5% acetonitrile containing 0.01% formic acid; Solvent B: acetonitrile. The gradient was shown 0-0.5 min: 2% solvent (B); 0.5-2.5 min: 2% solvent B to 95% solvent (B); 2.5-4.0 min: 95% solvent (B); 4.0-4.2 min: 95% solvent (B) to 2% solvent B; 4.2-6.0 min: 2% solvent (B).

Experimental Details

Example 1

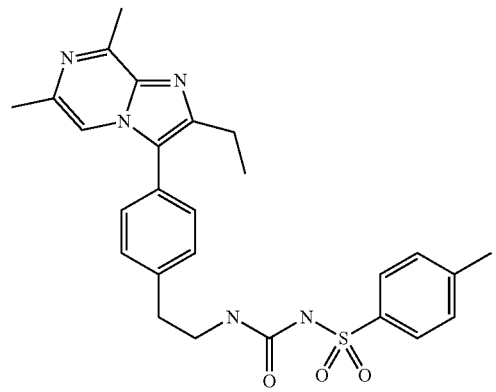

Compound A

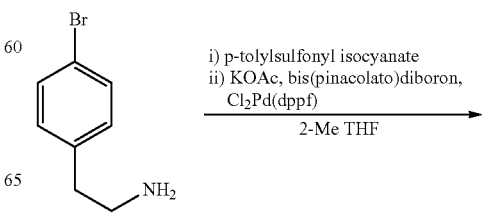

i) p-tolylsulfonyl isocyanate
ii) KOAc, bis(pinacolato)diboron, $Cl_2Pd(dppf)$
2-Me THF

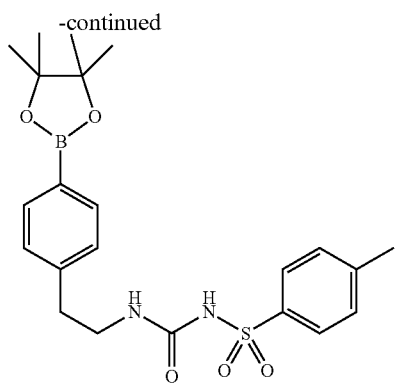

4-methyl-N-((4-(4,4,5,5-tetramethyl-1,3,2-dioxaborolan-2-yl)phenethyl)carbamoyl)benzenesulfonamide Reaction run in a 12 L 4 neck round bottom flask equipped with a thermowell, reflux condenser and N$_2$ inlet. To a cooled (<8° C.) solution of 4-bromophenethyl amine (291 g, 1.45 mol) in 2-MeTHF (5.82 L, 20 vol) was added p-tolylsulfonyl isocyanate (222 mL, 1.45 mol) at a rate that kept the internal temperature below 15° C. After internal temperature began cooling again (~5 min.), the ice bath was removed and reaction was allowed to stir at room temperature. After 16 h, it was noticed that the tubing attaching the stir shaft to the overhead stirrer failed. The failed piece of equipment was replaced, and the resultant mixture was allowed to stir for 22 h at room temperature. The reaction atmosphere was flushed with a stream of nitrogen for 20 min. before potassium acetate (428 g, 4.36 mol) was added. The mixture was degassed by bubbling N$_2$ through it for 2.5 h. Bis(pinacolato)diboron (443 g, 1.75 mol) and Cl$_2$Pd(dppf).CH$_2$Cl$_2$ (59.4 g, 72.7 mmol) were added. The reaction atmosphere was flushed with nitrogen for 15 min. before the mixture was further degassed by bubbling nitrogen through it for 45 min. Reaction was heated to 80° C. for 19 h under an atm. of N$_2$. Activated charcoal (303 g) was added and heating at 80° C. continued for 2 h before internal temperature was adjusted to 40° C. The warm (40° C.) mixture was filtered on a Buchner funnel and rinsed with 2-Me THF (5.82 L). The organic solution was extracted 3×1.94 L 10% aq. NaOH and pH of combined alkaline aq. fractions was adjusted to 5.03 (measured with a 3 point calibrated pH meter) with 6 molar aq. HCl (2.8 L) and 10% aq. NaOH (157 mL). The aq. layer and glassware were extracted 3×1.94 L EtOAc. The combined organic fractions were washed 1×1.94 mL saturated aq. NaCl, dried with Na$_2$SO$_4$ filtered and stored at room temperature for 9 h. The organic solution was concentrated in vacuo to give 681 g of a black tar that was stored at room temperature for 63 h. Tar was dissolved in hot (65° C.) EtOAc (1.36 L, 2 vol) and transferred to a 4 neck 12 L round bottom flask equipped with an overhead stirrer, addition funnel and thermowell coupled to a J-KEM/heating mantel. Internal temperature was adjusted to 65° C. and hot (65° C.) heptane (3 L, 4.4 vol) was added (over 45 min.) until solids were observed forming. The solution was seeded and the temperature of the J-KEM was adjusted to 55° C. Once internal temperature cooled to 55° C., stirring was continued for 1 h before additional hot (55° C.) heptane (475 mL) was added (over 40 min.) until solids were observed forming. Solution was seeded and the temperature of the J-KEM was adjusted to 45° C. After 25 min. a white suspension was observed and internal temperature was observed to be 44° C. The power to the heating mantel was turned off and the mixture was allowed to slowly to room temperature while stirring. After 9 h the mixture was filtered on a Buchner funnel and solids were rinsed with heptane (2.4 L). The solids were left to dry in the Buchner funnel while the vacuum was still pulling air for 6 h to give 398 g of a white solid. The solid was found to be ~93% by weight (HPLC area @ 220 nm and calculated response factor). Actual amount of 4-methyl-N-((4-(4,4,5,5-tetramethyl-1,3,2-dioxaborolan-2-yl)phenethyl)carbamoyl)benzenesulfonamide was 370 g (57% yield) as a white solid. $^1$H NMR (400 MHz, CHLOROFORM-d) δ=7.78 (d, J=8.0 Hz, 2H), 7.55 (d, J=8.4 Hz, 2H), 7.27-7.16 (m, 4H), 6.61-6.54 (m, 1H), 3.55-3.48 (m, 2H), 2.84 (t, J=6.8 Hz, 2H), 2.44 (s, 3H), 1.36 (s, 12H). LC/MS RT=1.35 min., 445.2 [M+H]$^+$

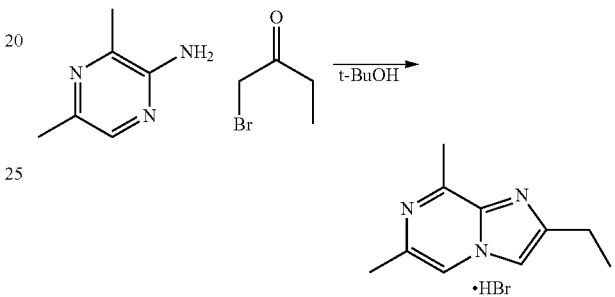

2-ethyl-6,8-dimethylimidazo[1,2-a]pyrazine HBr salt

To a solution of 2-amino-3,5-dimethyl pyrazine (112 g, 0.910 mol) in t-BuOH (1.7 L, 15 vol) was added 1-bromo-2-butanone (175 mL, 80% by weight, 1.36 mol). Reaction was heated to 80° C. for 19 h before the solution was cool to 30° C. and diluted with MTBE (1.7 L). Suspension was filtered on a Buchner funnel and solids rinsed with heptane (1.2 L). Filter cake was dried in the Buchner funnel under vacuum for 2 h to give 179 g of 2-ethyl-6,8-dimethylimidazo[1,2-a]pyrazine HBr salt (77%) as a pink solid. $^1$H NMR (400 MHz, DMSO-d$_6$) δ=8.58 (s, 1H), 8.23 (s, 1H), 2.89 (q, J=7.6 Hz, 2H), 2.83 (s, 3H), 2.50 (s, 3H), 1.32 (t, J=7.6 Hz, 3H).

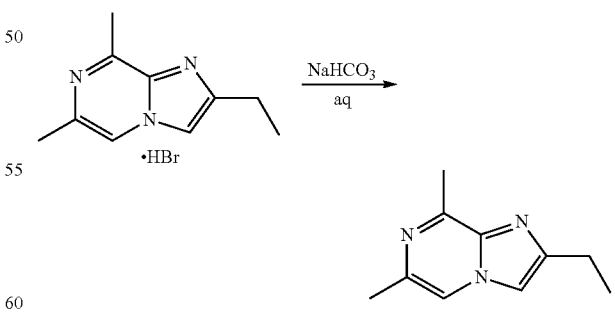

2-ethyl-6,8-dimethylimidazo[1,2-a]pyrazine

To a solution of saturated aq. NaHCO$_3$ (1.7 L) was added 2-ethyl-6,8-dimethylimidazo[1,2-a]pyrazine HBr salt (173 g, 674 mmol) portion wise over 3 min. The reaction was stirred at room temp for 30 min. before reaction was diluted with EtOAc (1 L) and saturated aq. NaCl (1 L). The organic layer was separated and the aq. layer was extracted 2×1 L EtOAc. The combined organic layers were washed 1×1 L saturated aq. NaCl, dried with Na$_2$SO$_4$, filtered and concentrated in vacuo to give 85.8 g of 2-ethyl-6,8-dimethylimidazo[1,2-a]pyrazine. The aq. fraction was re-extracted 3×1 L EtOAc and the combined organic fractions were washed 1×1 L saturated aq. NaCl, dried with Na$_2$SO$_4$, filtered and concentrated in vacuo to give an additional 29.7 g of 2-ethyl-6,8-dimethylimidazo[1,2-a]pyrazine. Total of 116 g (98%) of 2-ethyl-6,8-dimethylimidazo[1,2-a]pyrazine was isolated. $^1$H NMR (400 MHz, CHLOROFORM-d) δ=7.71 (s, 1H), 7.34 (s, 1H), 2.91-2.84 (m, 5H), 2.46 (d, J=0.8 Hz, 3H), 1.36 (t, J=7.6 Hz, 3H). LC/MS RT=0.19 min., 176.2 [M+H]$^+$

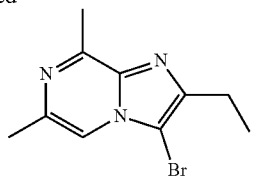

3-bromo-2-ethyl-6,8-dimethylimidazo[1,2-a]pyrazine

To a solution of 2-ethyl-6,8-dimethylimidazo[1,2-a]pyrazine (116 g, 659 mmol) in AcOH (1.73 L, 15 vol) was added bromine (33.8 mL, 659 mmol). Reaction stirred at room temperature for 1 h then concentrated in vacuo to remove 1.2-1.4 L of acetic acid. Slurry was diluted with water (0.7 L) to obtain a solution. The pH was adjusted (measured with a 3 point calibrated pH meter) from 1.11 to 7.12 with aq. NaOH (3.0 L, 10% by wt). The aq. solution was extracted 3×1 L EtOAc and the combined organic fractions were washed 1×500 mL saturated aq. NaCl, dried with Na2SO4, filtered and concentrated in vacuo to give 164 g of 3-bromo-2-ethyl-6,8-dimethylimidazo[1,2-a]pyrazine (98%). 1H NMR (400 MHz, CHLOROFORM-d) δ=7.70 (s, 1H), 2.90-2.82 (m, 5H), 2.53 (s, 3H), 1.35 (t, J=7.6 Hz, 3H). LC/MS RT=0.61 min., 256.2 [M+H]$^+$.

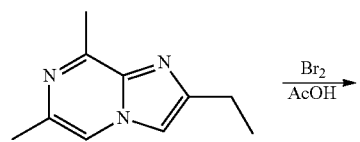

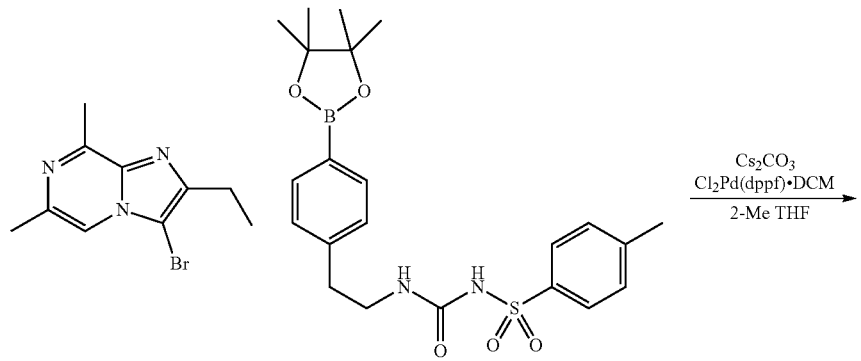

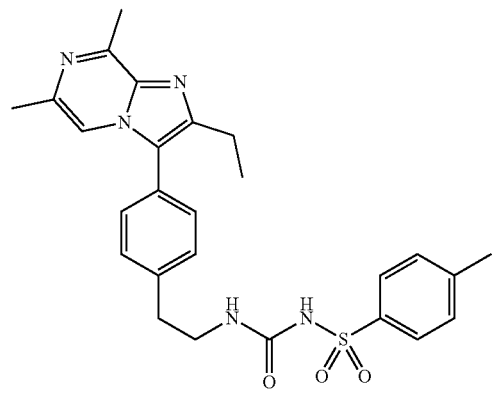

13 mol % pinacol
2.7 mol % EtOAc
1.5 mol % i-PrOH
2983 ppm Pd
APS-458

1-[2-[4-(2-ethyl-6,8-dimethyl-imidazo[1,2-a]pyrazin-3-yl)phenyl]ethyl]-3-(p-tolylsulfonyl)urea Reaction run in a 4 neck 12 L round bottom flask equipped with an overhead stirrer, thermowell, reflux condenser and $N_2$ inlet. A solution of 3-bromo-2-ethyl-6,8-dimethylimidazo[1,2-a]pyrazine (171 g, 99.7% by wt, 671 mmol) and 4-methyl-N-((4-(4,4,5,5-tetramethyl-1,3,2-dioxaborolan-2-yl)phenethyl)carbamoyl)benzenesulfonamide (322 g, 93% by weight, 671 mmol) in 2-Me THF (6 L, 20 vol) was degassed by bubbling $N_2$ through it for 5 hour. $Cs_2CO_3$ (658 g, 2.02 mol) and $Cl_2Pd(dppf)\cdot CH_2Cl_2$ (27.5 g, 33.6 mmol) were added and degassing was continued for 1 h. Reaction heated to reflux for 40 h before it was allowed to cool. When internal temperature dropped to 35° C., water (3 L) was added and mixture stirred until a biphasic solution was obtained. The 2-Me THF layer was separated and the pH of the aq. layer was adjusted (measured with a 3 point calibrated pH meter) from 9.66 to 5.03 with 6 molar aq. HCl (550 mL) and 1 molar aq. NaOH (55 mL). The aq. layer and glassware were extracted 4×2 L EtOAc. The EtOAc fractions were combined with the 2-Me THF fraction and the organic solution was washed saturated aq. NaCl (~25% volume of organic solution), dried with $Na_2SO_4$ (~100 g/L solution), filtered and concentrated in vacuo. The solution precipitated a black/brown solid during the last 6-8 L of solvent during the concentration and 455 g of a brown/black solid was obtained. Flask that contained solid was flushed with nitrogen, sealed with a septum and stored at room temperature for 64 h. Isolated solids were transferred to a 3 neck 5 L round bottom flask equipped with an overhead stirrer and thermowell coupled to a heating mantel. The solid was suspended in i-PrOH (1.1 L) and heated to 55° C. with stirring for 45 min. before the heating mantel was removed and allowed to cool to 27° C. over 1.5 h with stirring. The suspension was reheated to 55° C. for 45 min. before the heat was turned off to the heating mantel and the suspension allowed to slowly cool to room temperature with stirring over 15 h. The suspension was subjected to the same heat/cool cycle, with stirring, an additional 3 times before heat was turned off to heating mantel and mixture allowed to cool to room temperature over 17 h. Stirring was discontinued and suspension was filtered on a Buchner funnel. The isolated cake was rinsed with heptane (0.35 L). The top of the Buchner funnel was fitted with a sealed cover that fed nitrogen while the solid dried for 20 h under the vacuum applied. Isolated 266 g of 1-[2-[4-(2-ethyl-6,8-dimethyl-imidazo[1,2-a]pyrazin-3-yl)phenyl]ethyl]-3-(p-tolylsulfonyl)urea (80%) as a brown solid. The $^1$H NMR observed 13 mol % pinacol δ=1.20, along with 2.7 mol % EtOAc and 1.5 mol % i-PrOH contaminants. HPLC purity R.T.=5.66 min., 96.2584% at 220 nm and 98.9164% at 254 nm. $^1$H NMR (400 MHz, METHANOL-$d_4$) δ=7.83-7.77 (m, 3H), 7.39 (s, 4H), 7.33 (d, J=8.0 Hz, 2H), 4.10 (q, J=7.1 Hz, 1H), 3.95-3.89 (m, 1H), 3.43 (t, J=6.9 Hz, 2H), 2.89-2.76 (m, 7H), 2.39 (s, 3H), 2.35 (s, 3H), 2.02-2.00 (m, 1H), 1.28 (t, J=7.6 Hz, 3H), 1.20 (s, 2H), 1.15 (d, J=6.2 Hz, 1H). ICP-OES for Pd observed 2983 ppm Pd.

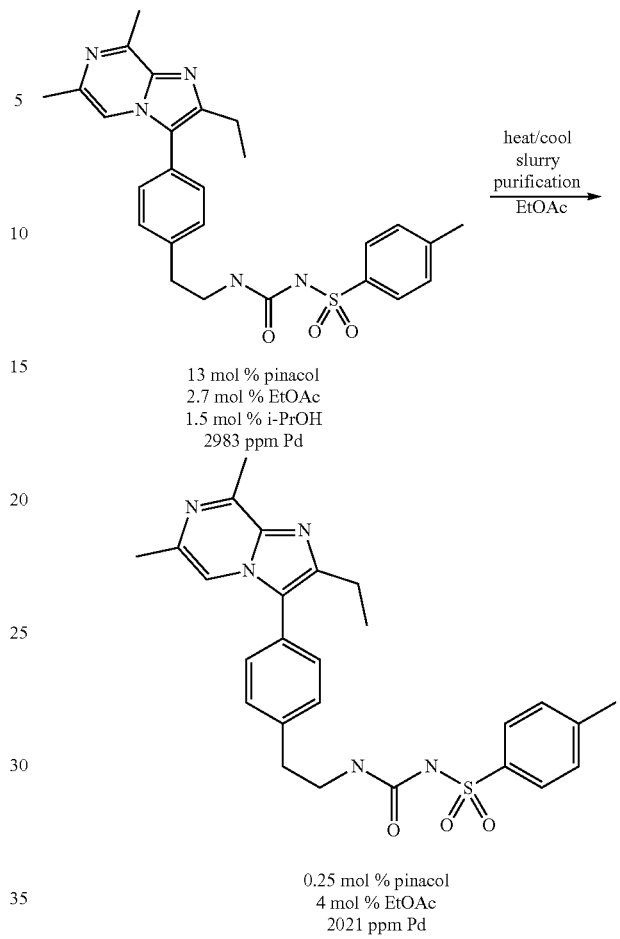

13 mol % pinacol
2.7 mol % EtOAc
1.5 mol % i-PrOH
2983 ppm Pd 0.25 mol % pinacol
4 mol % EtOAc
2021 ppm Pd

Slurry Purification

In a 3 neck 5 L round bottom flask equipped with an overhead stirrer and thermowell coupled to a heating mantel was added 1-[2-[4-(2-ethyl-6,8-dimethyl-imidazo[1,2-a]pyrazin-3-yl)phenyl]ethyl]-3-(p-tolylsulfonyl)urea (262 g) and EtOAc (2.61 L, 10 vol). Mixture was heated and stirred for 45 min at 50° C. before it was allowed to cool to 25° C. by removing heating mantel. Stirring was then continued at room temp for 45 min. before the heat cool cycle was repeated 2 additional times. The last cooling operation allowed to stir at room temp for 16 h. The heat cool cycle was repeated 2 additional times. The last cooling operation allowed to stir at room temp for 18 h. The mixture was filtered on a Buchner funnel. The top of the Buchner funnel was fitted with a sealed cover that fed nitrogen while the solid dried for 23 h under the vacuum applied. Isolated 206 g (79%) of 1-[2-[4-(2-ethyl-6,8-dimethyl-imidazo[1,2-a]pyrazin-3-yl)phenyl]ethyl]-3-(p-tolylsulfonyl)urea as a brown solid. The $^1$H NMR observed 4 mol % EtOAc and 0.25 mol % pinacol contaminants.

HPLC purity R.T.=5.67 min., 97.3690% at 220 nm and 99.1957% at 254 nm. ICP-OES for Pd observed 2021 ppm Pd. $^1$H NMR (400 MHz, METHANOL-$d_4$) δ=7.83-7.77 (m, 3H), 7.39 (s, 4H), 7.33 (d, J=8.2 Hz, 2H), 4.10 (q, J=7.1 Hz, 1H), 3.43 (t, J=7.0 Hz, 2H), 2.88-2.77 (m, 7H), 2.39 (s, 3H), 2.35 (s, 3H), 2.01 (s, 1H), 1.28 (t, J=7.6 Hz, 3H), 1.20 (s, 1H). LC/MS RT=0.91 min., 492.2 [M+H]$^+$. Anal Calcd for 1-[2-[4-(2-ethyl-6,8-dimethyl-imidazo[1,2-a]pyrazin-3-yl)phenyl]ethyl]-3-(p-tolylsulfonyl)urea (factoring in EtOAc and pinacol): C, 63.46; H, 5.97; N, 14.13; S, 6.47. Found: C, 63.41; H, 5.84; N, 13.84; S, 6.36. ICP-OES for Pd observed 2021 ppm Pd.

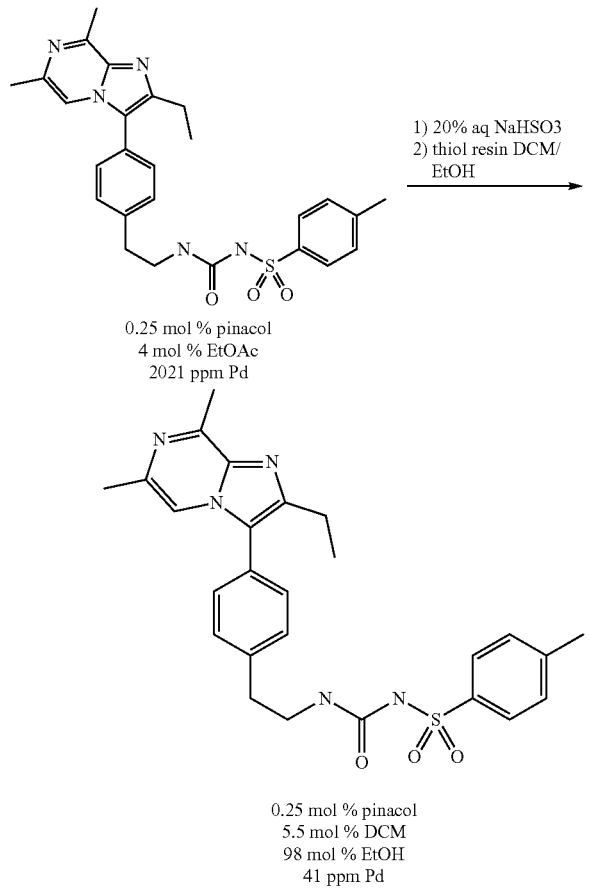

Palladium remediation of 1-[2-[4-(2-ethyl-6,8-dimethyl-imidazo[1,2-a]pyrazin-3-yl)phenyl]ethyl]-3-(p-tolylsulfonyl)urea NaHSO$_3$ (900 g) was dissolved in DI water (3.6 L) and a portion (2.71 L, 15 vol) was transferred into a 3 neck 5 L round bottom flask equipped with an overhead stirrer. 1-[2-[4-(2-ethyl-6,8-dimethyl-imidazo[1,2-a]pyrazin-3-yl)phenyl]ethyl]-3-(p-tolylsulfonyl)urea (186 g) was added and additional aq. NaHSO$_3$ (1 L) was used to rinse all the 1-[2-[4-(2-ethyl-6,8-dimethyl-imidazo[1,2-a]pyrazin-3-yl)phenyl]ethyl]-3-(p-tolylsulfonyl)urea into the aq. mixture in the flask. Mixture was vigorously stirred for 20 min before all the dry 1-[2-[4-(2-ethyl-6,8-dimethyl-imidazo[1,2-a]pyrazin-3-yl)phenyl]ethyl]-3-(p-tolylsulfonyl)urea was mixed within the aq. layer. Stirring continued for 2 h before the pH of the mixture was adjusted from 3.69 to 5.01 with aq. NaOH (215 mL, 2 molar). The mixture was extracted 3×5.7 L EtOAc and the organic layers were stored in amber 4 L bottles for 17 h. The organic layer was extracted 1×10% volume saturated aq. NaCl, dried with Na$_2$SO$_4$ (250 g/4 L solution), filtered through celite and concentrated in vacuo to give 173 g of a tan solid. A portion of the solid (657 mg) at this stage was separated and shipped for testing by ICP-OES for Pd. The remaining solid was dissolved in DCM/EtOH (3.45 L, 2:1) and transferred to a 3 neck 5 L round bottom flask equipped with an overhead stirrer. Silamet thiol (17.2 g, 1.36 mmol/g, 40-63 □m) was added and the mixture stirred at room temperature for 24 h. Mixture was filtered through a Buchner funnel and resultant solution was filtered through a Meisnner filter (0.45 mm). Meisnner filter was rinsed with DCM/EtOH (0.3 L, 2:1) and organic solution was concentrated in vacuo to give 183 g of 1-[2-[4-(2-ethyl-6,8-dimethyl-imidazo[1,2-a]pyrazin-3-yl)phenyl]ethyl]-3-(p-tolylsulfonyl)urea as a tan solid. The 1H NMR observed 5.5 mol % DCM and 98 mol % EtOH giving an actual yield of 167 g (90% recovery) of 1-[2-[4-(2-ethyl-6,8-dimethyl-imidazo[1,2-a]pyrazin-3-yl)phenyl]ethyl]-3-(p-tolylsulfonyl)urea. HPLC purity RT=5.81 min., 96.4616% at 220 nm and 99.0221% at 254 nm. ICP-OES for Pd, for sample obtained prior to treatment with thiol resin, observed 176 ppm Pd. ICP-OES for Pd, for final sample obtained, observed 41 ppm Pd. $^1$H NMR (400 MHz, METHANOL-d$_4$) δ=7.84-7.77 (m, 3H), 7.39 (s, 4H), 7.36-7.31 (m, 2H), 5.49 (s, 1H), 3.61 (q, J=7.1 Hz, 2H), 3.43 (t, J=7.0 Hz, 2H), 2.88-2.77 (m, 7H), 2.39 (d, J=0.8 Hz, 3H), 2.35 (s, 3H), 1.28 (t, J=7.6 Hz, 3H), 1.18 (t, J=7.1 Hz, 3H).

Abbreviations used herein fall within accepted use and should be interpreted accordingly.

All publications, patents and patent applications cited in this specification are incorporated herein by reference for the teaching to which such citation is used.

The specific responses observed may vary according to and depending on the particular active compound selected or whether there are present carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

The invention claimed is:

1. A process for making 1-[2-[4-(2-ethyl-6,8-dimethyl-imidazo[1,2-a]pyrazin-3-yl)phenyl]ethyl]-3-(p-tolylsulfonyl)urea or a salt thereof, comprising reacting 4-methyl-N-((4-(4,4,5,5-tetramethyl-1,3,2-dioxaborolan-2-yl)phenethyl)carbamoyl)benzenesulfonamide with 3-bromo-2-ethyl-6,8-dimethylimidazo[1,2-a]pyrazine.

2. A process for making a compound of Formula (II) or a salt thereof:

Formula (II)

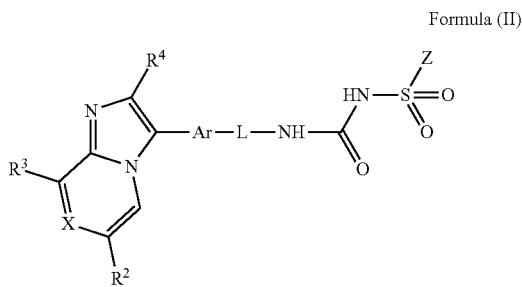

wherein:
X is N or $CR^1$, where $R^1$ is hydrogen, halogen, CN, $C_{1-3}$ alkyl, or $C_{1-3}$ haloalkyl;
$R^2$ is hydrogen, halogen, $C_{1-3}$ alkyl, $C_{1-3}$ haloalkyl, CN, aryl, or heteroaryl;
$R^3$ is hydrogen, halogen, $C_{1-3}$ alkyl, $C_{1-3}$ haloalkyl, or CN;
$R^4$ is hydrogen, $C_{1-3}$ alkyl, $C_{1-3}$ haloalkyl, $C_{3-6}$ cycloalkyl, heterocyclyl, heteroaryl, or aryl;
Z is phenyl substituted with $R^5$, where $R^5$ is hydrogen, halogen, CN, $C_{1-3}$ alkyl, $C_{1-3}$ haloalkyl, $C_{1-3}$ haloalkoxy, or $C_{1-3}$ alkoxy;
Ar is phenyl, pyridyl, or thiophenyl, each optionally substituted with one or more halogen, CN, $NO_2$, $NH_2$, $N(C_{1-3}$ alkyl$)_2$, OH, $C_{1-3}$ alkoxy, $C_{1-3}$ alkyl, or $C_{1-3}$ haloalkyl; and
L is $CH_2CH_2$, $CH_2CH_2CH_2$, or $OCH_2CH_2$, comprising:
  a. cyclizing a compound of formula (a):

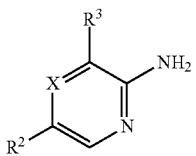

formula (a)

wherein:
X is N or $CR^1$, where $R^1$ is hydrogen, halogen, CN, $C_{1-3}$ alkyl, or $C_{1-3}$ haloalkyl;
$R^2$ is hydrogen, halogen, $C_{1-3}$ alkyl, $C_{1-3}$ haloalkyl, CN, aryl, or heteroaryl; and
$R^3$ is hydrogen, halogen, $C_{1-3}$ alkyl, $C_{1-3}$ haloalkyl, or CN;
  b. halogenating the resulting cyclized product to form a compound of formula (b):

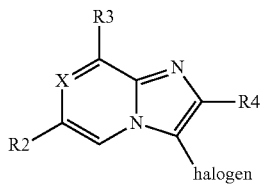

formula (b)

wherein $R^4$ is hydrogen, $C_{1-3}$ alkyl, $C_{1-3}$ haloalkyl, $C_{3-6}$ cycloalkyl, heterocyclyl, heteroaryl, or aryl; and
  c. treating a compound of formula (b) with a compound of formula (c):

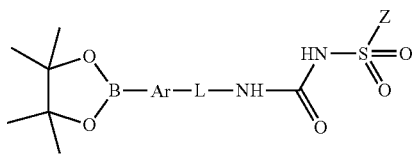

formula (c)

wherein
Z is phenyl substituted with $R^5$, where $R^5$ is hydrogen, halogen, CN, $C_{1-3}$ alkyl, $C_{1-3}$ haloalkyl, $C_{1-3}$ haloalkoxy, or $C_{1-3}$ alkoxy;
Ar is phenyl, pyridyl, or thiophenyl, each optionally substituted with one or more halogen, CN, $NO_2$, $NH_2$, $N(C_{1-3}$ alkyl$)_2$, OH, $C_{1-3}$ alkoxy, $C_{1-3}$ alkyl, or $C_{1-3}$ haloalkyl; and
L is $CH_2CH_2$, $CH_2CH_2CH_2$, or $OCH_2CH_2$,
to form a compound of Formula (II).

3. The process of claim 2, wherein
X is N,
$R^2$ is $C_{1-3}$ alkyl,
$R^3$ is $C_{1-3}$ alkyl,
$R^4$ is $C_{1-3}$ alkyl,
Ar is phenyl,
L is $CH_2CH_2$, and
Z is phenyl substituted with one $R^5$.

4. The process of claim 3, wherein $R^2$ is methyl, $R^3$ is methyl, $R^4$ is ethyl, Ar is unsubstituted phenyl, and $R^5$ is $C_{1-3}$ alkyl.

5. The process of claim 4, wherein $R^5$ is methyl.

6. The process of claim 5, wherein the compound of formula (c) is 4-methyl-N-((4-(4,4,5,5-tetramethyl-1,3,2-dioxaborolan-2-yl)phenethyl)carbamoyl)benzenesulfonamide.

7. The process of claim 6, wherein the compound of Formula (II) is 1-[2-[4-(2-ethyl-6,8-dimethyl-imidazo[1,2-a]pyrazin-3-yl)phenyl]ethyl]-3-(p-tolylsulfonyl)urea.

* * * * *